United States Patent [19]

Frisch

[11] 4,205,401
[45] Jun. 3, 1980

[54] MAMMARY PROSTHESIS WHICH RESISTS CAPSULAR CONTRACTURE

[75] Inventor: Eldon E. Frisch, Midland, Mich.

[73] Assignee: Dow Corning Corporation, Midland, Mich.

[21] Appl. No.: 909,406

[22] Filed: May 25, 1978

[51] Int. Cl.² .......................... A61F 1/24; A41C 3/10
[52] U.S. Cl. ...................................................... 3/36
[58] Field of Search ..................... 3/36, 1; 128/462

[56] References Cited

U.S. PATENT DOCUMENTS

| | | | |
|---|---|---|---|
| 3,559,214 | 2/1971 | Pangman | 3/36 |
| 3,663,968 | 5/1972 | Mohl et al. | 3/36 |
| 3,665,520 | 5/1972 | Perras et al. | 3/36 |
| 3,681,787 | 8/1972 | Perras | 3/36 |
| 3,852,833 | 12/1974 | Koneke et al. | 3/36 |
| 3,934,274 | 1/1976 | Hartley, Jr. | 3/36 |

FOREIGN PATENT DOCUMENTS 2199266  4/1974  France ........................................ 3/36

*Primary Examiner*—Ronald L. Frinks
*Attorney, Agent, or Firm*—Max J. Kenemore

[57] ABSTRACT

A surgically implantable mammary prosthesis comprises a sac containing a filler material. The filler material is present in an amount sufficient to give the sac a relatively low profile shape and a pliant, responsive nature. The prosthesis includes a restraining means for resisting the tendancy of tissue to form the prosthesis into a sphere. The restraining means functions reactive to tissue pressure and does not substantially reduce the pliant, responsive nature of the prosthesis.

9 Claims, 7 Drawing Figures

MAMMARY PROSTHESIS WHICH RESISTS CAPSULAR CONTRACTURE

BACKGROUND OF THE INVENTION

1. Field of the Invention

This invention relates generally to artificial body members and, more specifically, to surgically implantable breast prostheses.

2. Description of the Prior Art

Gel-filled silicone rubber breast prostheses have been employed for a number of years to maintain the natural appearance of the breast and for cosmetic purposes. A typical breast prosthesis of the gel-filled type is shown in U.S. Pat. No. 3,293,663 to Cronin.

While such a prosthesis when properly implanted effects augmentation of the breast, in time the capsule of fibrous tissue surrounding the prosthesis may cause a spherical contracture of the prosthesis into a relatively rigid and tense structure. As the tissues around the implant contract, the fixed volume of the silicone gel material within the container is forced into a shape having the smallest possible surface area, a sphere surrounded by essentially inelastic fibrous scar tissue. The hard spherical prosthesis results in an aesthetically undesirable breast.

Various solutions to this problem have been attempted. Hartley, Jr. (U.S. Pat. No. 3,934,274) discloses a double-walled prosthesis arranged so that some filler material can be released from the compartment between the double walls to reduce its size and to relieve the pressure of capsular contracture. The decompression procedure is accomplished by inserting a hypodermic needle through the breast and into the compartment. The filler material in the compartment is withdrawn through the needle. Such a procedure can be a great inconvenience to the patient. The Hartley, Jr. prosthesis has the additional disadvantage that it does not prevent reoccurance of capsular contraction.

Perras et al. (U.S. Pat. No. 3,665,520) discloses a prosthesis which has an extended shape and which includes a fabric material to increase the rigidity of the back wall of a prosthesis so that the combined shape and stiffness counteract the forces of tissue ingrowth. The prosthesis disclosed by Perras leaves room for improvement. The extension becomes firm and palpable with fibrous tissue ingrowth in some patients and therefore a non-extended shape would be more desirable. Further, it is desirable in many instances to use an implant in which the restraining means functions only in response to tissue pressure.

SUMMARY OF THE INVENTION

It is, therefore, the principal object of this invention to furnish a prosthetic device which resists the force of encapsulating tissue sufficiently to avoid taking on a spherical shape.

It is another object of the invention to overcome the disadvantages of the prior art.

These and other objects are accomplished by a mammary prosthesis which resists capsular contracture and which comprises a sac containing a filler and having a restraining means. The filler is present in an amount sufficient to give the sac a relatively low profile shape and a compliant, responsive nature over at least its broad surfaces. The restraining means is positioned or constructed within the sac or the sac wall and functions reactive to tissue pressure. The restraining means resists the tendency of the tissue to form the prosthesis into a sphere without substantially reducing the pliant, responsive nature of the prosthesis.

The restraining means is capable of resisting the distorting pressure of tissue of at least about 5 g/cm$^2$. In some embodiments the restraining means is a flexible member. In other embodiments the restraining means is a chamber containing a fluid under pressure.

BRIEF DESCRIPTION OF THE DRAWINGS

The invention is described below with reference to the drawings in which.

DETAILED DESCRIPTION

Figure 1:
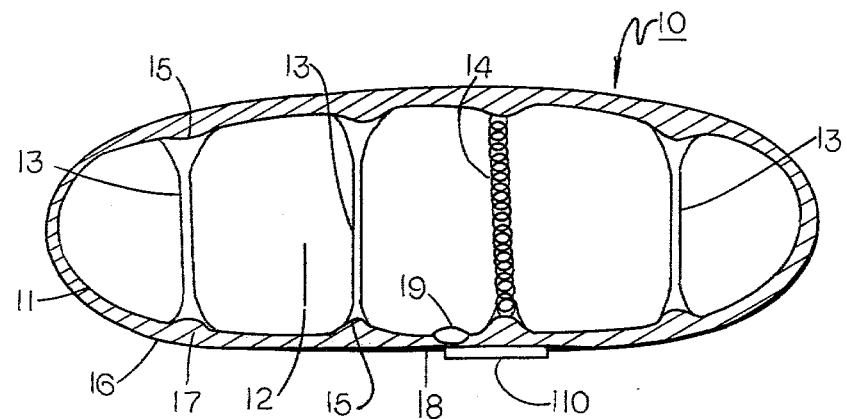
FIG. 1 shows schematically and in cross-section an embodiment in which the restraining means comprises a plurality of flexible members constructed within the sac.

Referring now specifically to FIG. 1 there is shown prosthesis 10 which includes sac 11 containing filler material 12.

Opposite sides of sac 11 are connected by restraining means 13 and 14 which are constructed within sac 11. Restraining means 13 and 14 cause sac 11 to have an uneven surface at their points of connection with sac 11, such as points 15.

Casing 16 is positioned over sac 11 and the space between casing 16 and sac 11 is filled with a cushioning gel material 17 having sufficient density that the uneven surface on sac 11 is not translated to casing 16.

Sac 11 and casing 16 are made from any useful material. Typical of useful materials are cellulose acetate, cellulose acetate butyrate, cellulose nitrate, crosslinked polyvinyl alcohol, polyurethanes, nylon 6, nylon 6.6, aromatic nylon, polyvinyl acetate, plasticized polyvinylacetate, polyvinyl butyrate, ethylene vinyl acetate copolymers, polyethylene, polypropylene polyisobutylene, polyvinyl chloride, plasticized polyvinylchloride, natural rubber, and synthetic elastomers including, for example, silicone rubber and polybutadiene.

Silicone rubber is a preferred membrane material for sac 11 and casing 16 because of its relative strength and flexibility and because of its well known compatibility by animal tissue. A preferred material is a medical grade silicone elastomer available from Dow Corning Corporation.

The thickness of the membrane which forms sac 11 and casing 16 can vary depending on such considerations as the overall size of sac 11 and the desired membrane strength. The membrane is typically from about 0.001 to about 0.020 inch (0.0254 mm to about 0.508 mm) thick.

Suitable filler materials 12 and gels 17 include, for example, saline solutions (at about 9 g/l.) and silicone gels. Such filler materials 12 and gels 17 are useful because of their compatibility with the body. Silicone gels are well known in the art and are more fully described in U.S. Pat. No. 3,020,260. Such gels are preferred because of the compliant, resilient nature they give to the prosthesis.

Sac 11 contains filler material 12 in an amount sufficient to give the prosthesis a pliant, responsive nature over at least its broad surfaces and a low profile shape. This is normally achieved by filling sac 11 to about ¾ of capacity.

Restraining means 13 and 14 are flexible members which are constructed within sac 11. Means 13 is a flexible elastomer strip of silicone rubber which connects the opposite sides of sac 11. Restraining means 14 is a spring which connects opposite sides of sac 11.

Both restraining means 13 and 14 are flexible so that they do not substantially reduce the pliant, responsive nature of the prosthesis over at least its broad surfaces. However, a uniform pressure applied around the surface of casing 16, such as the contractive pressure applied by tissue, will cause restraining means 13 and 14 to resist such pressure, preventing prosthesis 10 from being drawn into a sphere. Restraining means 13 and 14 operate reactive to tissue pressure.

The strength of restraining means 13 and 14 should be sufficient to resist the contractive pressure of body tissue. For normal implants, restraining means 13 and 14 should be able to withstand a stretching force adequate to develop a filler pressure of about 5 $g/cm^2$ before yielding significantly. Greater strengths are also useful, but relatively high strengths begin to make prosthesis 10 less and less pliant and responsive. Strengths of restraining means 13 and 14 greater than needed to retain shape at a filler pressure of about 70 $g/cm^2$ are not normally used.

Any suitable material which is flexible and sufficiently resistant to stretching is useful in making restraining means 13 and 14. Typical such materials include rubbers such as the rubbers useful in making sac 11 and casing 16, metal spring material and flexible filaments such as nylon fibers and Dacron fibers, both of which are available from du Pont.

The mixing of restraining means such as 13 and 14 in one prosthesis 10 is unusual and is illustrated to show that different types of restraining means are useful.

The prosthesis of FIG. 1 is manufactured by first forming sac 11 on a mandrel by dip-coating. Molding and vacuum coating are also well known in the art. After sac 11 is stripped from the mandrel, various points on the inner surface are connected by attaching the ends of restraining means 13 and 14 thereto. Attachment is normally by means of a silicone elastomer adhesive which is cured to form a bond between sac 11 and restraining means 13 and 14. However, any suitable attaching means can be used. An example of other suitable attachment is a loop of rubber material which is molded into the inner surface of sac 11.

The restraining means are attached by working through the opening (not shown) which is left in sac 11 when it was stripped from the mandrel.

Casing 16 is made by dip-coating a mandrel and heat curing. After curing, casing 16 is stripped from the mandrel, leaving a relatively small opening 18.

Sac 11 is folded to small dimensions and inserted into casing 16 through opening 18. A drop 19 of high strength silicone elastomer is placed on sac 11 near opening 18. The high strength elastomer forms a self sealing valve as taught in U.S. Pat. No. 3,600,718. A hypodermic needle is inserted through the skin of sac 11 at the location of drop 19, and sac 11 is partially filled with filler material 12. Sac 11 is not filled to its capacity but only an amount sufficient to give sac 11 a low profile shape and to give it a pliant responsive nature over its broad surfaces.

Seal 110 is placed over opening 18, and gel material 17 is inserted therethrough in an amount sufficient to support casing 16 around sac 11. Gel material 17 can be used to support casing 16 to any suitable degree of firmness; however, there should be at least sufficient gel material 17 to give casing 16 a relatively even exterior.

Figure 2:
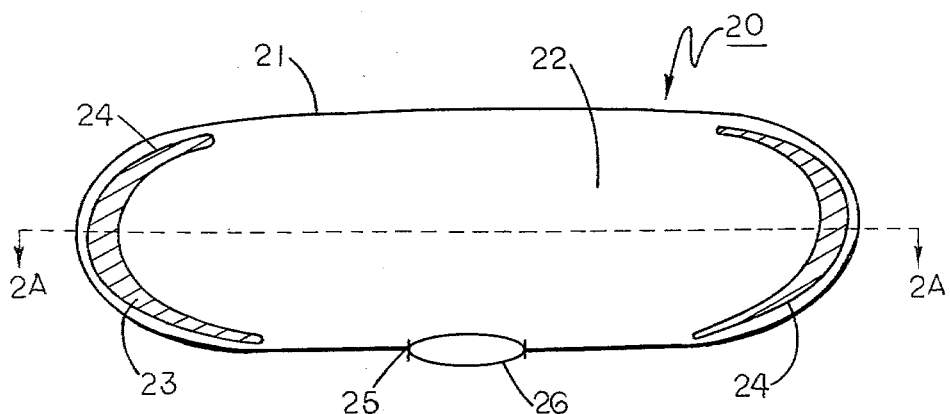
FIG. 2 shows schematically and in cross-section an embodiment in which the restraining means is a flexible member positioned within the sac.
Figure 2A:
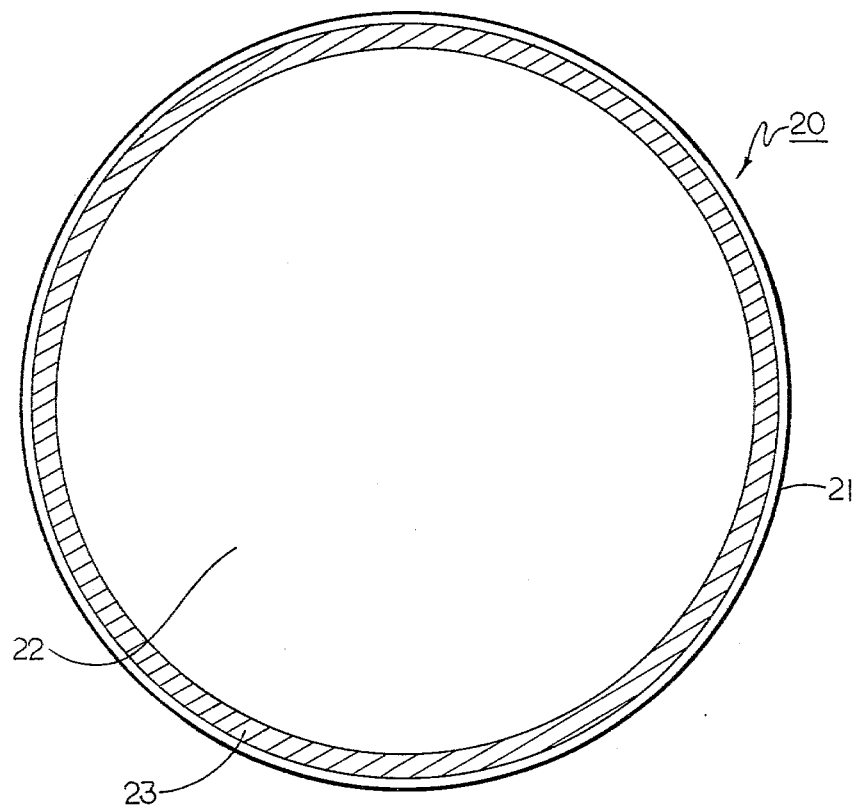
FIG. 2A shows schematically and in cross-section the embodiment of FIG. 2 along lines 2A—2A.

Referring more specifically to FIGS. 2 and 2A, there is shown another embodiment of the present invention wherein prosthesis 20 includes sac 21, filler material 22 and restraining means 23 which is positioned inside sac 21. Sac 21 and filler material 22 are similar to sac 11 and filler material 12 described in connection with FIG. 1.

Restraining means 23 is a flexible member which aids is giving sac 21 a low profile shape and resists the pressure of tissue contraction sufficiently that sac 21 is not drawn into a sphere. Restraining means 23 can be of any suitable shape and material. To be useful, means 23 should be relatively lightweight and flexible. It should be able to withstand a force equal to at least about 5 $g/cm^2$ before yielding.

As shown in FIG. 2, it is preferred that means 23 has tapered ends 24 which are not easily palpable after surgical implantation.

Prosthesis 20 is assembled by dipcoating and heat curing sac 21 over a mandrel. Sac 21 is stripped from the mandrel leaving a relatively small opening 25. Restraining means 23 is positioned in sac 21 by pushing it through opening 25. The materials suitable for making sac 21, as discussed in connection with FIG. 1 are normally stretchable. Means 23 can be positioned within sac 21 with as much ease as sac 21 is stripped from the mandrel.

Opening 25 is then sealed with seal 26 and filler material 22 is injected through the seal. Although any suitable seal can be used, seal 26 is normally a high density (self-sealing) silicone elastomer which is subsequently heat cured.

It is to be understood that many variations of the restraining means shown in FIGS. 2 and 2A are useful. For example, means 23 could be a disk having an enlarged edge and a barbell profile or it could be shaped like a shallow cup having its bottom positioned over seal 26.

Figure 3:
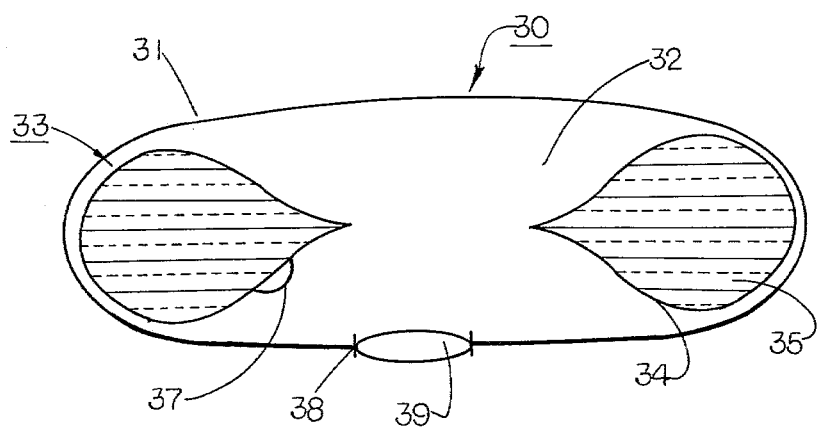
FIG. 3 shows schematically and in cross-section an embodiment in which the restraining means is a chamber containing a fluid under pressure positioned in the sac.
Figure 3A:
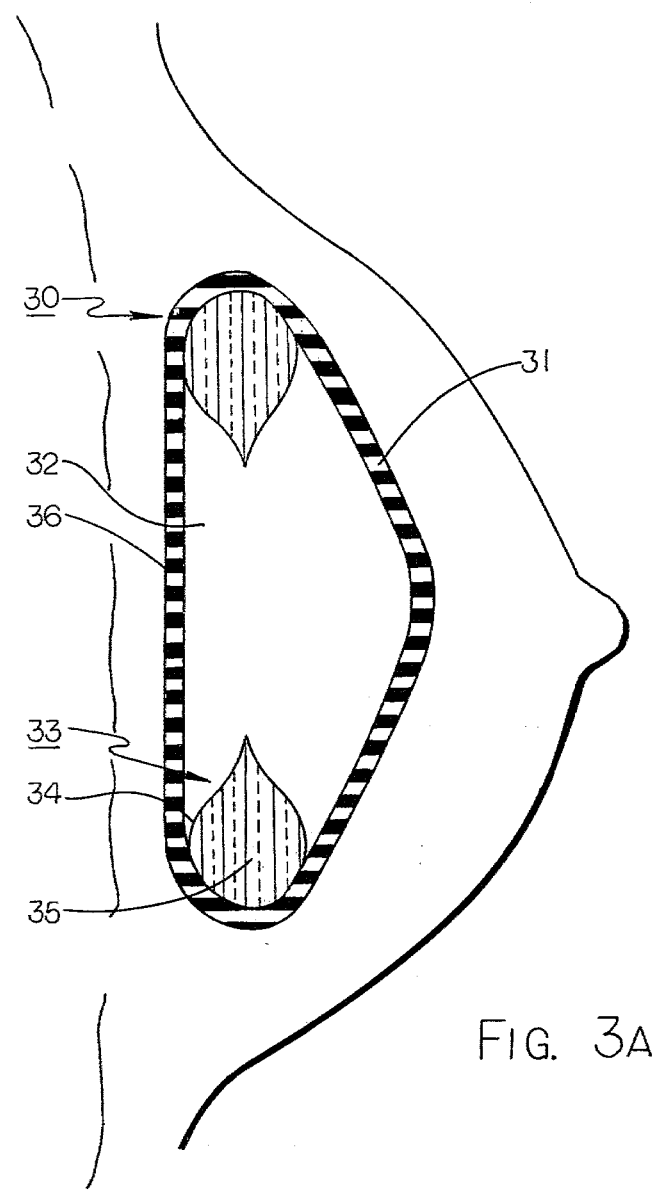
FIG. 3A shows schematically and in cross-section the embodiment after having been surgically implanted.

Referring more specifically to FIGS. 3 and 3A there is shown prosthesis 30 which includes sac 31 and filler material 32. Suitable sacs and fillers are discussed above.

Restraining means 33 includes an inner chamber 34 and a pressured filler material 35. As shown in FIG. 3 filler material 32 fills sac 31 sufficiently to give sac 31 a low profile shape and a pliant, responsive nature. Restraining means 33 is positioned in sac 31 so that it fits loosely within the profile. Pressured filler material 35 in restraining means 33 has sufficient pressure to resist a compressive force of at least about 5 g/cm² before flexing.

FIG. 3A shows prosthesis 30 after being surgically implanted to augment a breast. Capsular tissue 36, which is greatly exaggerated for illustrative purposes, is shown to be attempting to force sac 31 into a sphere. Sac 31 has been drawn up snugly against restraining means 33. The resistance to flexing which is given to chamber 34 by pressured filler material 35 is sufficient to resist the force exerted by tissue capsule 36.

Capsular contracture of the prosthesis is thus avoided. The embodiment of FIGS. 3 and 3A is especially desirable because restraining means 33 is not palpable as a hard object after surgical implantation.

Prosthesis 30 is manufactured by first forming chamber 34. Chamber 34 is made in the shape of sac 31 and is draped over a first mandrel so that the edges extend beyond the mandrel. A mating mandrel is placed over the sac so that the center of the sac is pressed between the mandrels. The mandrels are heated so as to seal the opposite sides of the sac together.

A high strength drop 37 of silicone elastomer is placed on the inside curve of the portion of sac 34 which extends beyond the mandrel to form a self-sealing valve. A hypodermic needle is used to puncture sac 34 under drop 37 and gel 35 in injected to the desired pressure. A pressure of at least about 5 cm H₂O is generally established; however, gel 35 can be under even greater pressure if desired.

Sac 31 is formed by dip coating a mandrel and heat curing. Sac 31 is stripped from the mandrel, leaving hole 38. Hole 38 is stretched to allow positioning of restraining means 33 in sac 31 as shown in FIG. 3.

Hole 38 is sealed with seal 39, and filler material is injected through seal 39 until sac 31 is supported sufficiently to have a low profile shape and a pliant, responsive character.

Figure 4:
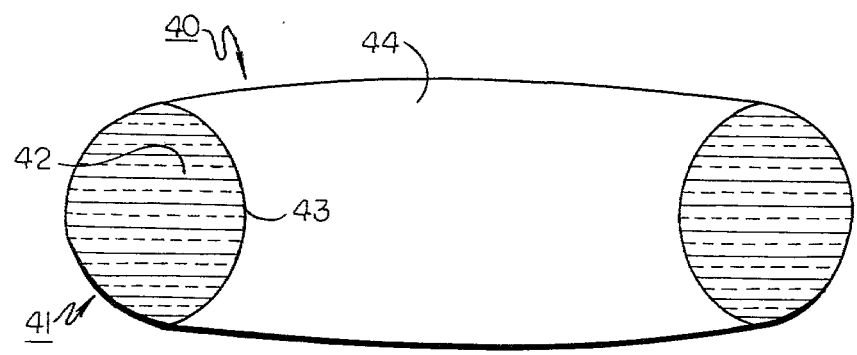
FIG. 4 shows schematically and in cross-section an embodiment wherein the restraining means is a chamber containing a fluid under pressure constructed within the sac.

Referring more specifically to FIG. 4 there is shown prosthesis 40 which has restraining means 41 constructed within it. Restraining means 41 includes pressured gel 42 in chamber 43. The main body of prosthesis 40 is filled with filler material 44 such as filler material 32 of FIG. 3.

Prosthesis 40 is manufactured by first forming the chamber for filler material 44 by dipcoating and heat curing a silicone elastomer onto a cylindrical mandrel. An ellipsoid mandrel is also dipcoated and heat cured with a silicone elastomer. The outer curve from the elipsoid mandrel is cut away and attached to the edges of the cylindrical mandrel to form the chamber for pressured gel 42. Attachment is with a silicon elastomer adhesive. The construction is then stripped from the cylindrical mandrel, sealed and hypodermically filled.

Figure 5:
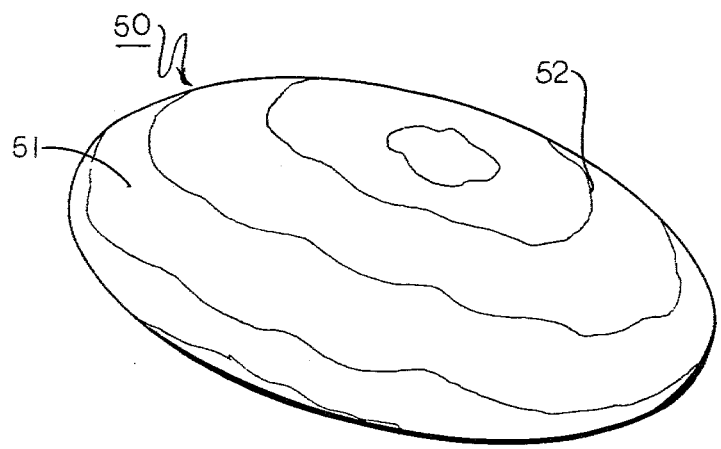
FIG. 5 shows in perspective view an embodiment in which the restraining means is a plurality of filaments in the sac wall.

Referring more specifically to FIG. 5 there is shown prosthesis 50 which includes sac 51 containing sufficient filler material to give it a relatively low profile and a pliant responsive nature. Restraining means 52, constructed in the walls of sac 51, is a plurality of flexible filaments. Although filaments 52 are flexible, they are not elastic. Filaments 52 are arranged laterally around the walls of prosthesis 50 and are embedded in sac 51. The filaments allow flexing of sac 51 so that prosthesis 50 is pliant and responsive. However, the filaments will resist the efforts of capsular tissue to force prosthesis 50 into a spherical shape.

Prosthesis 50 is made by molding the upper and lower halfs separately. Filaments 52 are placed in the molds in the desired arrangement, and material to form sac 51 is poured over the filaments. The sac material is normally a heat curable silicone elastomer. After heat curing, the prosthesis halves are stripped from the molds and joined by an adhesive. Sac 51 is filled with a suitable filler material by hypodermic injection as described above.

It is to be understood that filaments 52 can have any arrangement which will prevent prosthesis 50 from being drawn into a sphere. For example, filament 52 could be a single filament which is spirally embedded in one or both halves of sac 51.

It will be apparent to those skilled in the art upon reading the above disclosure that the embodiments of FIGS. 1, 3, 3A, 4 and 5 can be filled during surgical implantation. Filling of the prosthesis at that time with a filler material or with a pressured gel can be done hypodermically through the incision and has the advantage of requiring a smaller incision.

The present invention has been disclosed in the above teachings and drawings with sufficient clarity and conciseness to enable one skilled in the art to make and use the invention, to know the best mode for carrying out the invention and to distinguish it from other inventions and from what is old. Many variations and obvious adaptations of the invention will readily come to mind, and these are intended to be contained within the scope of the invention as claimed below.

That which is claimed is:

1. A surgically implantable mammary prosthesis which resists capsular contracture, the prosthesis comprising: (a) a sac containing
   (b) a filler material in an amount sufficient to give the sac a relatively low profile shape and a pliant, responsive nature over at least its broad surfaces, and
   (c) ring-shaped restraining means positioned so as to function reactive to tissue pressure to resist the tendency of tissue to form the prosthesis into a sphere without substantially reducing the pliant, responsive nature of the prosthesis.

2. The prosthesis of claim 1 wherein the restraining means is capable of resisting a pressure of at least about 5 g/cm².

3. The prosthesis of claim 1 wherein the restraining means is a tube containing filler material under pressure.

4. The prosthesis of claim 3 wherein the tube is continuous with the sac.

5. The prosthesis of claim 3 wherein the tube is loosely positioned within the sac.

6. The prosthesis of claim 1 wherein the restraining means is a flexible member loosely positioned within the sac.

7. The prosthesis of claim 1 wherein the restraining means is a plurality of filaments embedded in the walls of the prosthesis.

8. The prosthesis of claim 1 wherein the sac is formed of silicone rubber.

9. The prosthesis of claims 1 or 3 wherein the filler material is a silicone elastomer gel.

* * * * *

UNITED STATES PATENT AND TRADEMARK OFFICE
CERTIFICATE OF CORRECTION

PATENT NO. : 4,205,401
DATED : June 3, 1980
INVENTOR(S) : ELDON E. FRISCH

It is certified that error appears in the above-identified patent and that said Letters Patent are hereby corrected as shown below:

Column 3, line 64, after the word "attachment" insert

--means--.

Column 4, line 67, after the word "the" insert --low--.

Column 5, line 51, "silicon" should read --silicone--.

Signed and Sealed this

Sixth Day of January 1981

[SEAL]

Attest:

SIDNEY A. DIAMOND

Attesting Officer          Commissioner of Patents and Trademarks